United States Patent
Smits et al.

[11] Patent Number: 5,545,207
[45] Date of Patent: Aug. 13, 1996

[54] MEDICAL ELECTRICAL LEAD HAVING STABLE FIXATION SYSTEM

[75] Inventors: Karel F. A. A. Smits, Oirsbeek, Netherlands; Ivan M. P. G. Bourgeois, Heusy, Belgium

[73] Assignee: Medtronic, Inc., Minneapolis, Minn.

[21] Appl. No.: 295,334

[22] Filed: Aug. 24, 1994

[51] Int. Cl.$^6$ .................................................. A61N 1/05
[52] U.S. Cl. ............................................................ 607/130
[58] Field of Search .......................... 128/642; 607/119, 607/120, 122, 125, 126, 128–131

[56] References Cited

U.S. PATENT DOCUMENTS

| | | |
|---|---|---|
| 4,010,758 | 3/1977 | Rockland et al. |
| 4,058,128 | 11/1977 | Frank et al. ............................ 607/130 |
| 4,144,890 | 3/1979 | Hess . |
| 4,149,542 | 4/1979 | Thorén . |
| 4,177,818 | 12/1979 | De Pedro . |
| 4,258,725 | 3/1981 | O'Neill . |
| 4,294,258 | 10/1981 | Bernard ................................. 128/642 |
| 4,469,104 | 9/1984 | Peers-Trevarton . |
| 4,506,680 | 3/1985 | Stokes . |
| 4,572,605 | 2/1986 | Hess .................................... 339/177 R |
| 4,577,642 | 3/1986 | Stokes . |
| 4,603,704 | 8/1986 | Mund et al. . |
| 4,606,118 | 8/1986 | Cannon et al. ......................... 29/825 |
| 4,677,989 | 7/1987 | Robblee . |
| 4,711,251 | 12/1987 | Stokes . |
| 4,773,433 | 9/1988 | Richter et al. . |
| 4,784,160 | 11/1988 | Szilagyi . |
| 4,784,161 | 11/1988 | Skalsky et al. . |
| 4,819,661 | 4/1989 | Heil, Jr. et al. . |
| 4,819,662 | 4/1989 | Heil, Jr. et al. . |
| 4,898,173 | 2/1990 | Daglow et al. . |
| 4,972,848 | 11/1990 | Di Domenico et al . |
| 5,007,435 | 4/1991 | Doan et al. . |
| 5,070,605 | 12/1991 | Daglow et al. ........................ 29/842 |
| 5,085,218 | 2/1992 | Heil, Jr. et al. ...................... 128/642 |
| 5,143,090 | 9/1992 | Dutcher et al. . |
| 5,154,183 | 10/1992 | Kreyenhagen et al. . |
| 5,330,525 | 7/1994 | Proctor ............................... 607/130 |
| 5,397,343 | 3/1995 | Smits ................................... 607/130 |

FOREIGN PATENT DOCUMENTS 0134367  3/1985  European Pat. Off. ............... 607/130

Primary Examiner—William E. Kamm
Assistant Examiner—Jeffrey R. Jastrzab
Attorney, Agent, or Firm—Michael J. Jaro; Harold R. Patton

[57] ABSTRACT

An epicardial lead having an electrode extending from the bottom thereof in combination with an anchoring system adapted to secure the lead to the heart without the use of complex procedures or tools. In particular the lead achieves stable fixation through the provision of a flexible member moveable between a first position and a second position and a pair of fixation members connected to said flexible member, each fixation member having a distal end and a root, each flexible member connected to the electrode mounting at a point beyond the tip portion of the fixation member.

12 Claims, 5 Drawing Sheets

5,545,207

MEDICAL ELECTRICAL LEAD HAVING STABLE FIXATION SYSTEM

BACKGROUND OF THE INVENTION

1. Field of the Invention

This invention relates to medical leads for providing electrical signals to a human organ, such as a heart, and more particularly, to an epicardial lead having a stable fixation system adapted for quick attachment without extensive operative procedures to suture or connect the lead to the heart surface.

2. Description of the Prior Art

Heart leads are used to provide an electrical connection between a pulse generator and a patient's heart. In a great majority of the cases where the pulse generator is implanted within a patient on a permanent basis, transvenous leads are used, wherein the lead is introduced into the heart through a convenient vein. This procedure avoids the requirement of having to establish direct access to the heart itself. Such leads also avoid the trauma of actually inserting the lead into the heart wall. The endocardial lead as disclosed in U.S. Pat. No. 4,506,680 to Stokes, for example, has proven very successful for use in a large majority of cases.

In a certain percentage of cases, however, it is deemed necessary or desirable to use an external or epicardial lead, wherein the electrode or electrodes are mechanically inserted into the epicardium. In this arrangement, it is necessary the insertion be made with a minimum of trauma but yet be absolutely secure so that good electrical contact is maintained with the heart. Historically, one form of such an epicardial lead has involved actually suturing the lead onto the heart wall to thereby insure the required security. This has the great disadvantage, however, of increasing the complexity of the operative procedure required to implant such a lead.

To overcome the difficulties and complexities presented by use of a sutured epicardial lead, the medical device industry has developed a screw-in epicardial lead. This lead consists of a helical coil which is screwed into the heart wall. Examples of such a lead are disclosed in U.S. Pat. No. 5,154,183 to Kreyenhagen et al., U.S. Pat. No. 5,143,090 to Dutcher et al., U.S. Pat. No. 5,085,218 to Heil Jr. et al. and U.S. Pat. No. 4,010,758 to Rockland et al. This type of lead, however, requires sufficient room to approach the heart wall from a direction more or less perpendicular to the surface to enable the helical coil to be screwed directly into the heart muscle. Even if a perpendicular approach is not required, the physician must still have sufficient access to the heart so as to be able to push and rotate the helical coil tip into the epicardium.

An alternative to a screw-in lead may be seen in U.S. Pat. No. 4,177,818 to DePedro which discloses an epicardial electrode constructed from a pliable material and having a series of fixation prongs. This lead, however, requires the use of a tool or instrument to deform the lead body back against itself in order to attach it to the heart surface. A variation on such a flexible epicardial lead is disclosed in U.S. Pat. No. 4,144,890 to Hess which shows a lead which must be flexed forward with a tool, rather than backward, against itself in order to insert it into the epicardium.

While these leads have enjoyed a reasonable success to date, they still offer many possibilities of improvement. The heart is an organ constantly undergoing movement. This motion presents at least two difficulties. First, constant motion will tend to cause an object to be expelled from the heart. The fixation mechanisms of these leads have not been shown to be wholly secure. In addition, while providing stable fixation, it is also important that the lead not damage the tissue to thereby provoke formation of scar tissue. Scar tissue affects the electrical properties of the tissue and thus may inhibit the performance of the lead. This is especially likely in cases where the lead creates a relatively large amount of scar tissue.

SUMMARY OF THE INVENTION

It is an object of the invention to provide an epicardial lead which permits the securing of such lead to either the atrial or ventricular epicardium of a patient's heart or to another organ of the patient, which lead is simple to use, provides a highly stable fixation, and does not require an elaborate engaging tool.

It is another object of this invention to provide an epicardial lead which may be attached to a patient's heart without the need for suturing, and which is of a design which may be easily and reliably fixed to the heart without requiring additional procedures heretofore used to gain access to the heart to attach a sutured or screw-in type lead.

It is a further object of this invention to provide a lead adopted for quick and secure manual fixation to a patient's heart so that when said lead is fixed it is not subject to lateral, vertical or rotational movement relative to the heart.

It is a further object of this invention to provide a lead which permits the electrode to first contact the heart tissue and permit the desired site of stimulation and sensing to be detected without first causing the fixation mechanism to engage the heart.

In accordance with the above objects there is provided an epicardial lead having an electrode extending from the bottom thereof in combination with an fixation system whereby the lead is secure and stable with respect to movement due to lateral, vertical or rotational movement of the heart wall itself. In the preferred embodiment the epicardial lead comprises a lead body having two fixation members, each fixation member attached to a flexible member, the flexible member in turn attached to the lead housing. The flexible member features an integral spring to maintain its positioning with respect to the lead housing. Each fixation member is shaped to cooperate with the flexible member so that forces induced on the fixation members by intrinsic heart movement, i.e. contractions, do not lessen the placement of the fixation members in the heart tissue.

3

Figure 8:
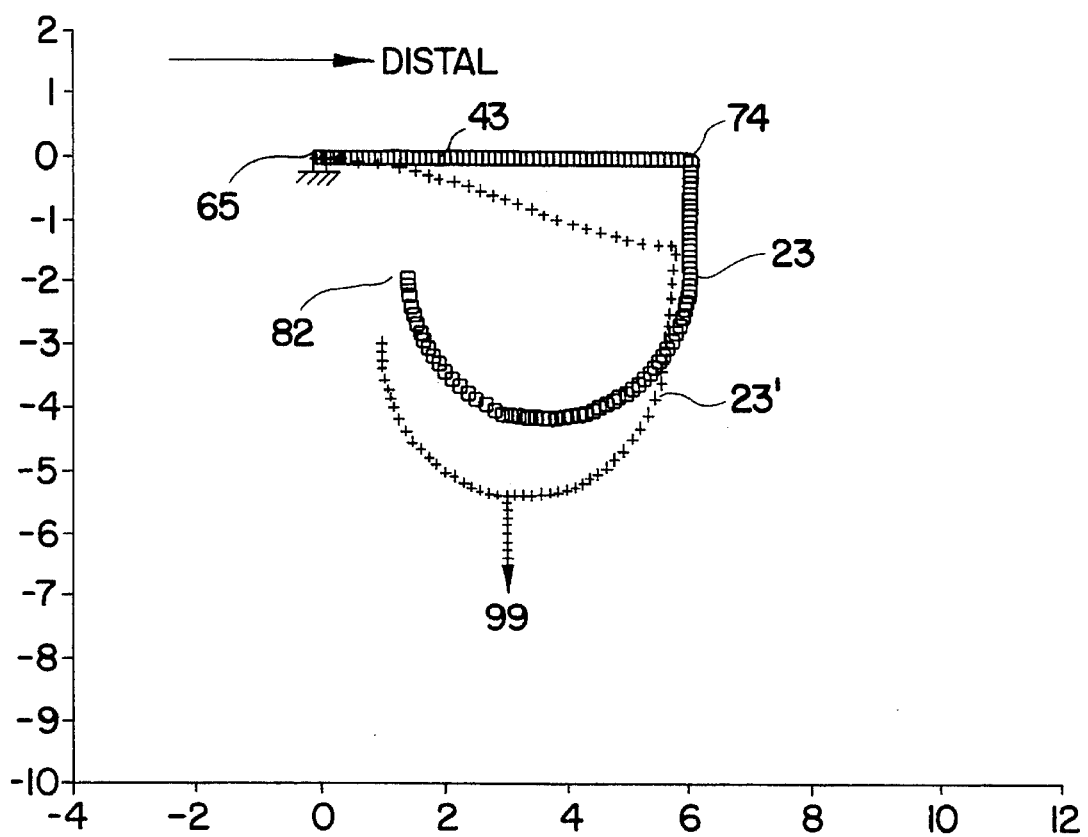

FIG. 8 is a plotting of distortion of an alternative design of a fixation member caused by a force from heart contraction.

Figure 9:
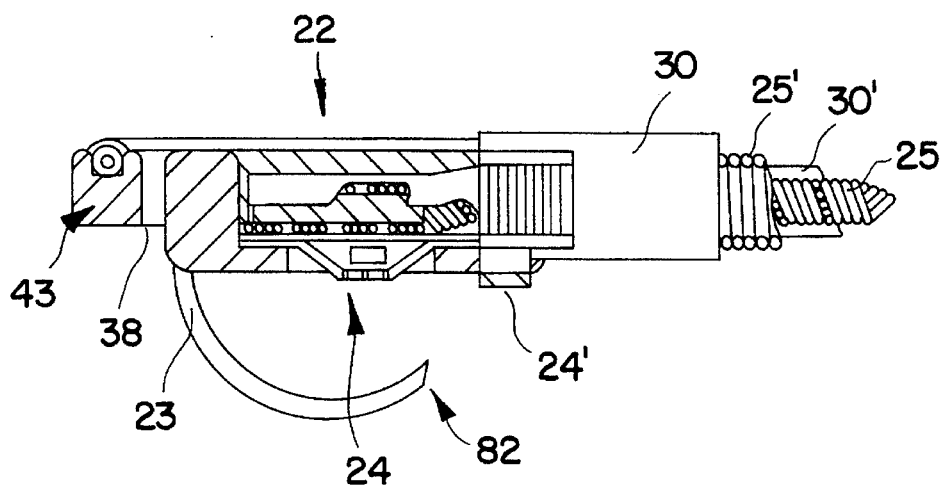

FIG. 9 is a side cross-sectional view of a bipolar lead head according to the present invention.

Figure 10:
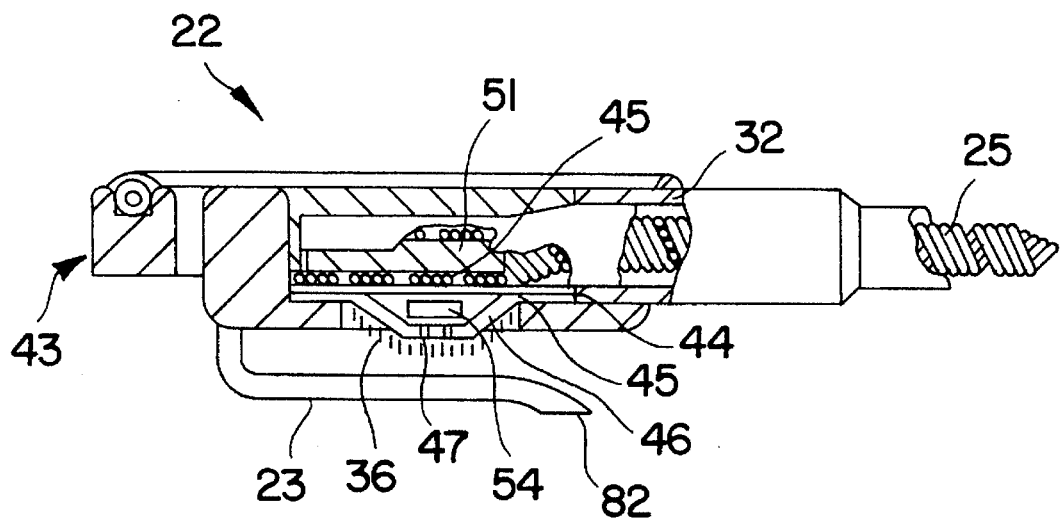

FIG. 10 is a side cross-sectional view of an alternate embodiment of the present invention.

Figure 11:
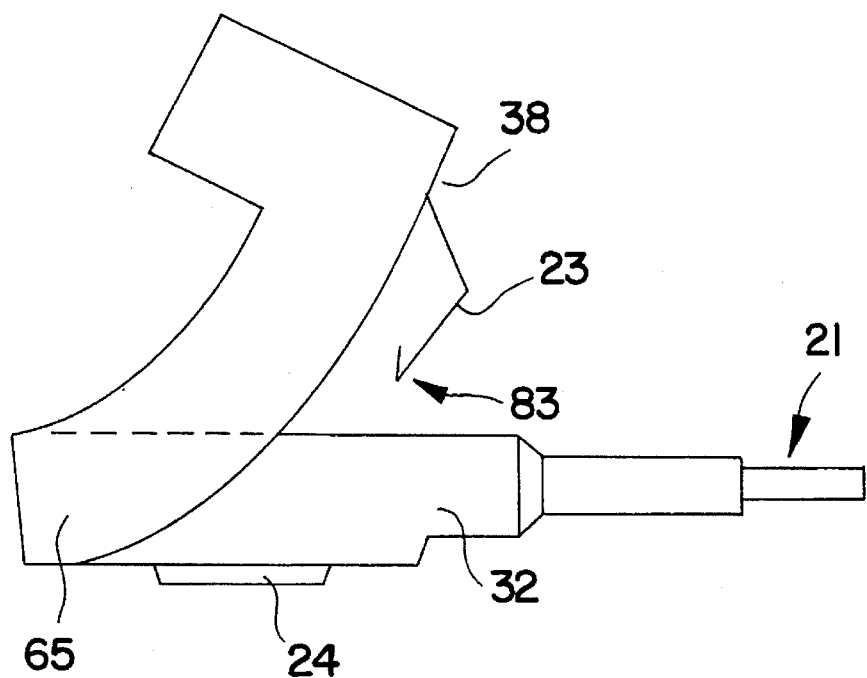

FIG. 11 is a side cross-sectional view of an alternate embodiment of the present invention having the flexible member retracted so the lead head may be attached to the heart.

The drawings are not necessarily to scale.

DESCRIPTION OF THE PREFERRED EMBODIMENTS

Figure 1:
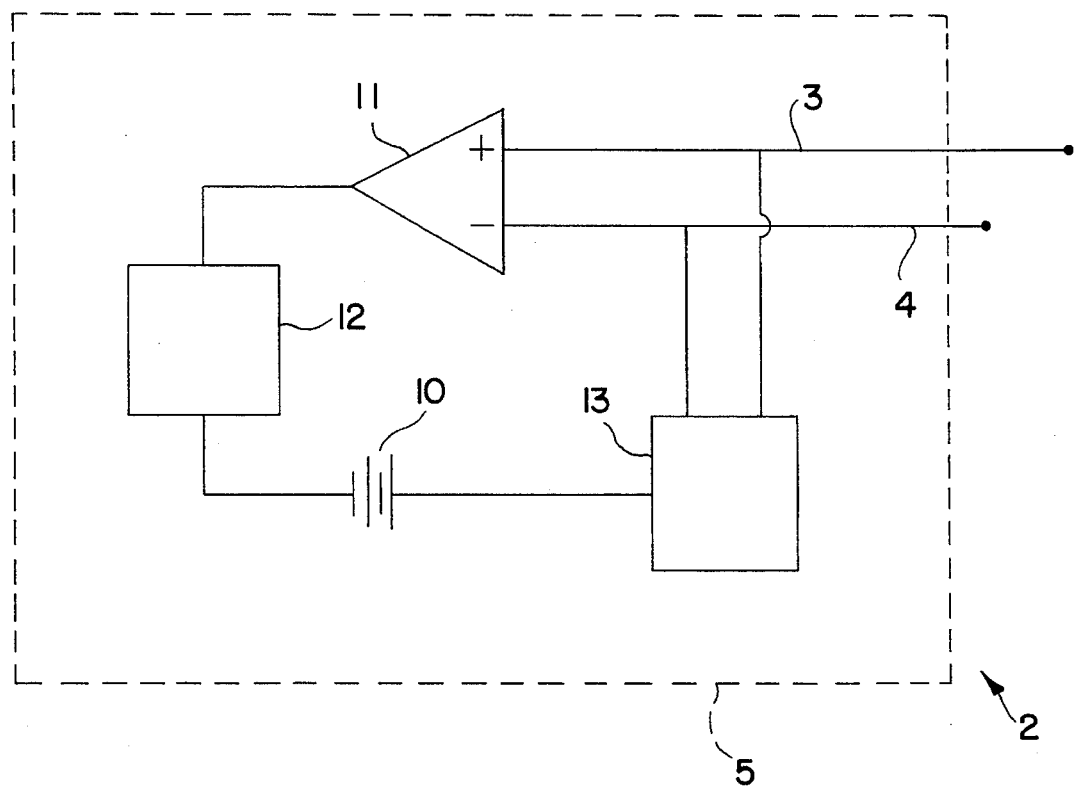
FIG. 1 is a schematic view of a lead in use with an implantable pulse generator system.

FIG. 1 is a schematic view of a lead in use with a pacing system 2, showing conductors 3, 4 electrically connected to an implantable pulse generator 5. Implantable pulse generator 5 is constructed from a battery 10, a sense amp 11, a microprocessor 12, and an output amp 13. Through such a pacing system 2, the lead of the present invention may be used to electrically stimulate and sense body tissue, such as a heart.

Figure 2:
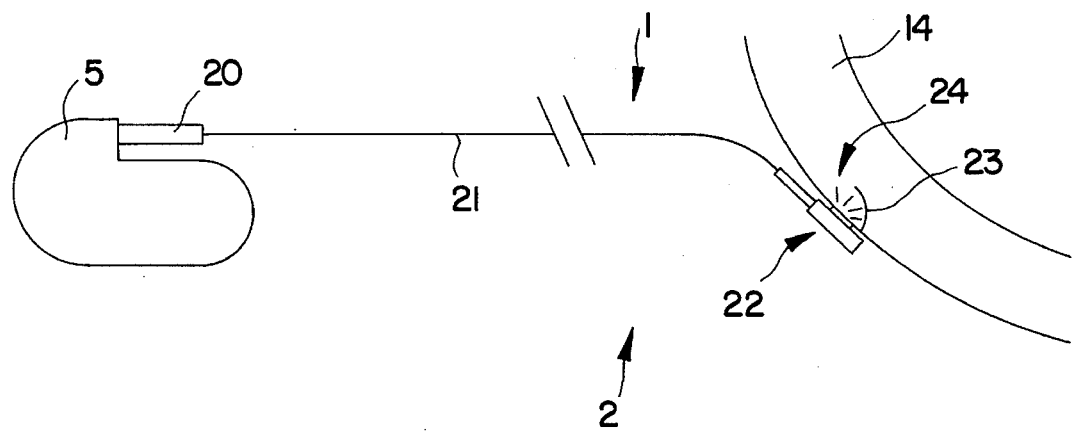
FIG. 2 is a lead according to the present invention in use with an implantable pulse generator system.

FIG. 2 shows a lead 1 according to the present invention in use as part of a pacing system 2 and implanted within a heart 14. Lead 1, as seen, has essentially five parts or sections: connector 20, lead body 21, lead head 22, fixation members 23 and electrode 24.

Although a preferred embodiment and alternate embodiments thereof of a lead constructed according to the present invention are shown in the FIGS. 3–11 the same numerals will be employed to describe the same or equivalent elements of each embodiment of the lead.

Figure 3:
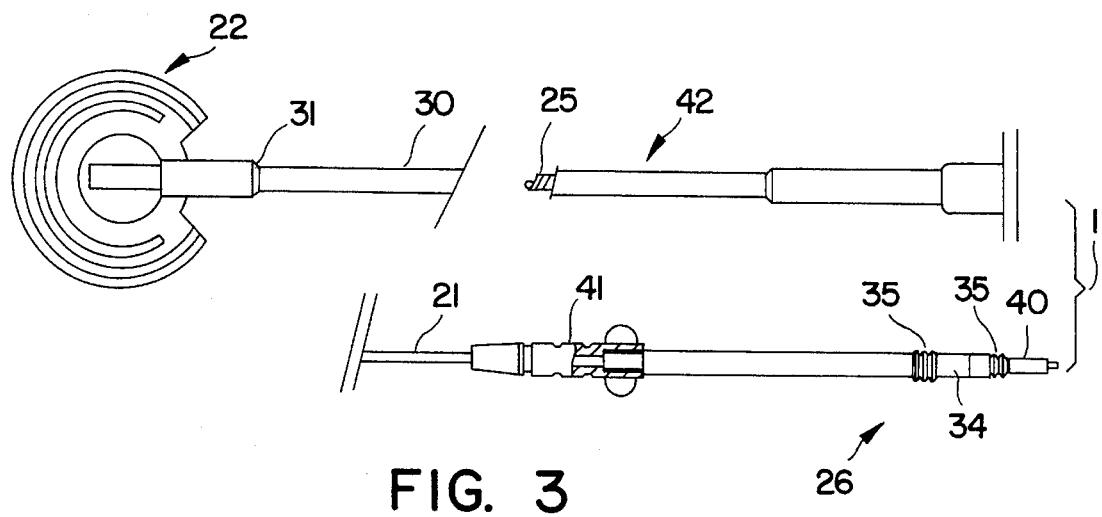
FIG. 3 is a plan view of a lead constructed in according to the present invention.

Referring to FIG. 3, a lead 1 constructed according to the present invention is shown. It should be noted, however, the relative proportions of lead 1, and especially lead head 22 depicted in FIG. 3 are not to scale. As seen, lead 1 comprises elongated lead body 21 and lead head 22. Lead body 21 comprises a standard arrangement of a coiled conductor 25 or conductors (partially shown in cutaway) encased in a suitable insulating cover 30 of a biocompatible material, such as silicone or a urethane material. Although in the preferred embodiment a coiled conductor is featured, other types of conductor may also be used, such as bundled stranded wire. At distal end 31 of elongated lead body 21, as shown, lead head 22 is located.

Figure 4:
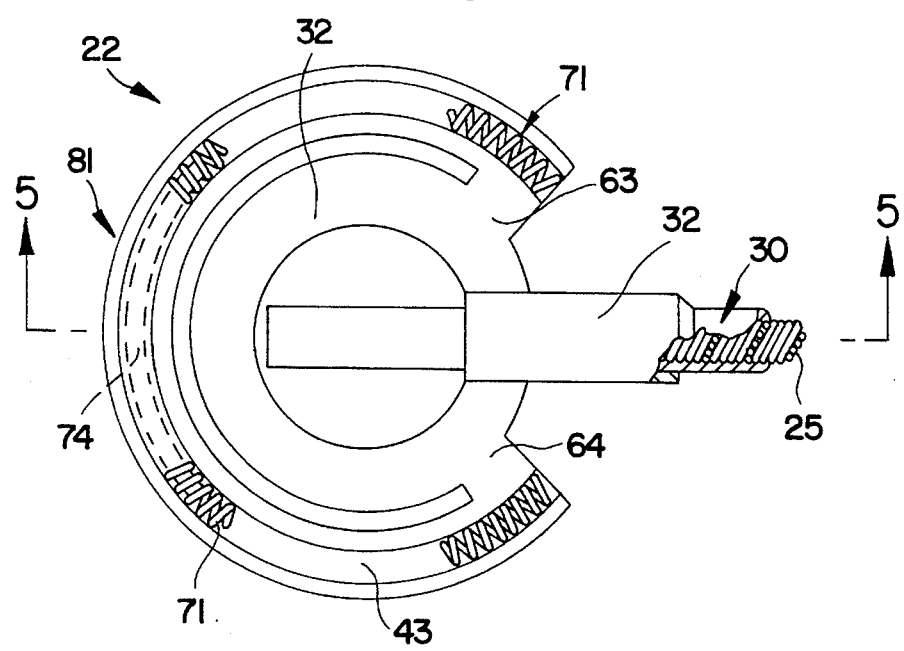
FIG. 4 is a plan view of the top side of a lead head according to the present invention.
Figure 5:
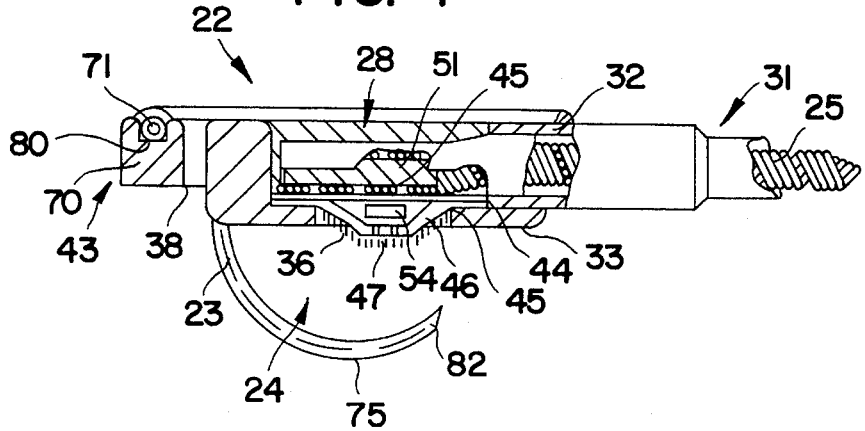
FIG. 5 is a side cross-sectional view of a lead head according to the present invention.
Figure 7:
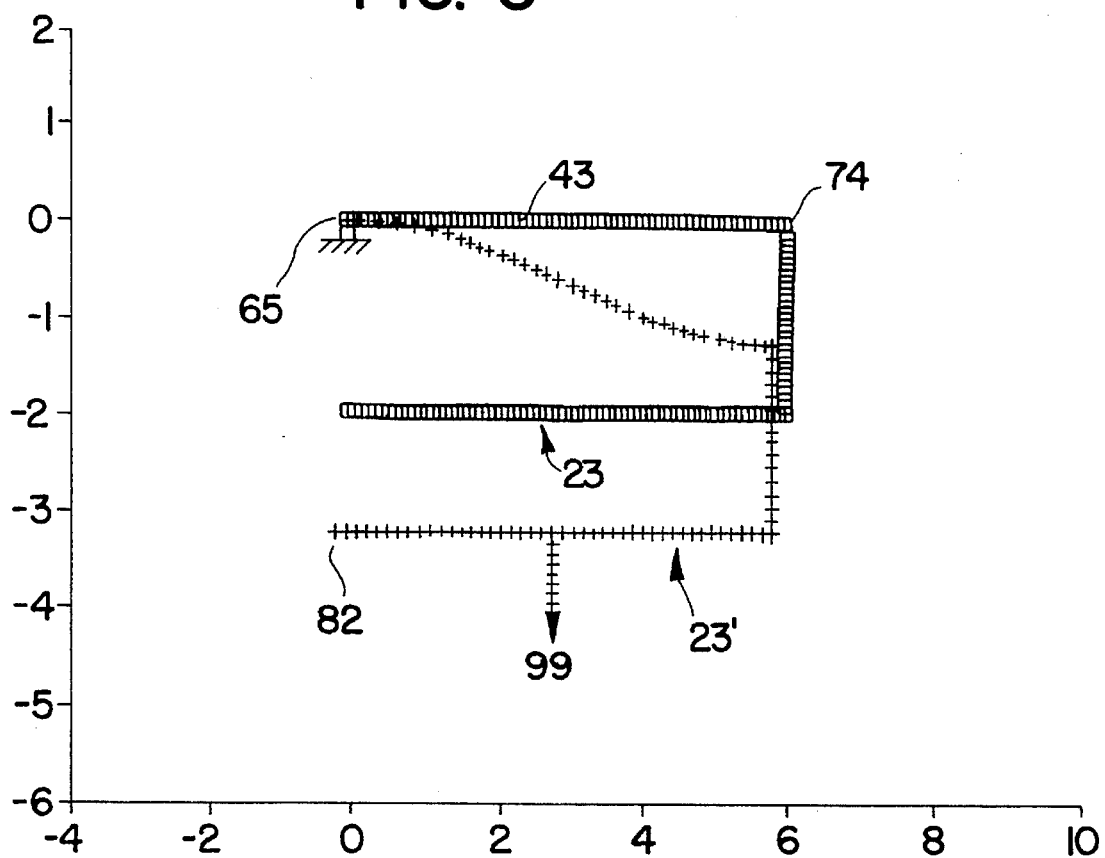
FIG. 7 is a plotting of distortion of the fixation member caused by a force from heart contraction.

As seen in FIG. 4 lead head 22 is constructed from electrode mounting 32 and flexible member 43. Electrode mounting 32 has electrode 24 extending from its bottom surface 33 as best seen in FIG. 5. Flexible member 43 has a pair of fixation members 23 extending from bottom surface 38 (only a single fixation member 23 may be seen, however, due to the plan view.) Fixation member 23 may be shaped for the specific application of the lead, for example, a ventricular lead having arcuate fixation member 23 is depicted in FIG. 5 and an atrial lead having straight fixation member 23 is depicted in FIG. 10. Fixation member 23 cooperates with flexible member 43 so that forces exerted by the contracting heart on fixation member 23, illustrated by the arrow 99, do not tend to dislodge fixation member 23 from heart tissue, as illustrated by FIGS. 7 and 8. As seen fixation member 23 is moved by force 99 to the position shown as 23'. Preferably each fixation portion 75 of fixation member 23 in the ventricular lead is arcuate in shape, to thereby minimize tissue injury during implantation, although other shapes, such as the straight shape (for an atrial application) seen in FIG. 10, may also be used. In addition, retaining barbs or prongs 83 could also be incorporated along fixation member 23, as seen in FIG. 11.

Lead 1 includes an elongated lead body 21 comprising a length of coiled conductor 25 and an insulative cover 30 as is well known in the art. Insulative cover 30 may be fabricated of any flexible biocompatible and biostable insulator especially silicone rubber or polyurethane.

At proximal end 26 of elongated lead body 21, terminal assembly 34 is adapted to couple lead 1 to a pulse generator 5. Terminal assembly 34 is provided with sealing rings 35 and a terminal pin 40, all of a type known in the art.

An anchoring sleeve 41 (shown partially in cross-section) slides over insulative cover 30 and serves as a point for suturing elongated lead body 21 to body tissue in a fashion known in the art. Anchoring sleeve 41 and terminal assembly 34 are preferably fabricated of silicone rubber, although they may also be constructed of any other suitable biocompatible material known in the art.

Lead body 21 features reduced diameter portion 42 to provide greater flexibility proximate lead head 22 as is well known in the art. The specific design and construction of elongated lead body 21 and terminal assembly 34 are not within the scope of the present invention. Further detail and description of the construction of an elongated lead body 21 and terminal assembly 34 suitable for use with the present invention may be seen, for example, in Daglow et al. U.S. Pat. Nos. 5,070,605 and 4,898,173; Doan et al., U.S. Pat. No. 5,007,435; Hess, U.S. Pat. No. 4,572,605; Peers-Trevarton, U.S. Pat. No. 4,469,104; and O'Neil, U.S. Pat. No. 4,258,725, all incorporated herein by reference.

As best seen in FIG. 5 lead head 22 is fixed to distal end 31 of elongated lead body 21. Lead head 22 comprises electrode mounting 32 and flexible member 43. Electrode mounting 32 is constructed from polyurethane, although other biocompatible materials may also be used such as silicone. Once electrode 24 is suitably mounted within electrode mounting 32, interior portion 28 may be backfilled to maintain electrode 24 in place. Backfill of interior portion 28 may be accomplished with any suitable biocompatible material, in the preferred embodiment with polyurethane.

Mounted along bottom surface 33 of electrode mounting 32, as seen in FIG. 5, is electrode 24. Electrode 24 is preferably constructed from a platinum-iridium alloy. Electrode 24 may further be constructed from a porous platinum covered with platinum black 36. Although platinum-iridium alloy is the preferred material for electrode 24, it may additionally include or be made entirely from various other materials, including but not limited to such materials as palladium, titanium, tantalum, rhodium, iridium, carbon, vitreous carbon and alloys, oxides and nitrides of such metals or other conductive materials. Of course, some materials are incompatible with others, such as a platinum with a titanium, and may not be effectively used together. The limitations of specific materials for use with others is well known in the art.

Electrode 24 is suitably connected to coiled conductor 25 to provide the necessary mechanical and electrical contact between electrode 24 and terminal assembly 34. As seen in FIG. 5 electrode 24 is connected to coiled conductor 25 through use of crimp core 51. Once coiled conductor 25 is crimped about crimp core 51, coiled conductor 25 may be attached to top plate 44 through a series of spot welds, generally indicated as 45. Further attached by spot welds to the underside of top plate 44 is electrode disk 46 so as to have an inner cavity 49 defined therein. As seen core 54 is located therein. Electrode disk 46 is porous through holes 47, thereby permitting core 54 to communicate with the exterior of electrode 24. Electrode disk 46 is covered on its exterior by a porous coating of platinum black 36.

Core 54 functions as a monolithic controlled release device and may be constructed from polyurethane or any other appropriate polymer. Through such materials core 54 may preferably be loaded with an anti-inflammatory drug, e.g., asteroid such as dexamethasone sodium phosphate, which will elute from core 54 through electrode 24 and into surrounding body tissue to reduce inflammatory response and tissue ingrowth. Further description of the construction, use and advantages of a monolithic controlled release device incorporating steroid with an implantable lead may be seen, for example in Stokes, U.S. Pat. No. 4,506,680 and related Medtronic U.S. Pat. Nos. 4,577,642; 4,606,118; 4,711,251 and 4,972,848 all incorporated herein by reference.

Electrode 24 is thereby preferably configured to allow the steroid or other anti-inflammatory agent to be eluted through and/or around in order to reach the tissue proximate thereto and reduce the acute and chronic inflammation occasioned by the cellular foreign body and physical irritation response to the lead head 22. As described in Stokes, U.S. Pat. No. 4,506,680 and related Medtronic U.S. Pat. Nos. 4,577,642; 4,606,118 and 4,711,251, mentioned above, asteroid eluting electrode is fabricated from a body compatible electrically conductive material with or without specific steroid eluting passages but generally with a porous structure either throughout the body of the electrode or at its surface. The porosity of the electrode surface or body provides a large surface area for sensing whereas the overall dimension or shape of the exposed electrode defines a comparatively smaller surface area for stimulation. The porous structure thus presents a microscopic (or "fractal") large surface area for sensing and a macroscopic or geometrically measured very small surface area for stimulation. Acceptable electrode materials and the associated fabrication techniques employed to achieve the microporous structure, as well as the porosity of that structure are all set forth in the aforementioned prior art patents and in the Richter et al., U.S. Pat. No. 4,773,433; Heil Jr. et al., U.S. Pat. No. 4,819,661; Thoren et al., U.S. Pat. No. 4,149,542; Robblee, U.S. Pat. No. 4,677,989; Heil Jr. et al., U.S. Pat. No. 4,819,662; Mund et al., U.S. Pat. No. 4,603,704; Skalsky et al., U.S. Pat. No. 4,784,161 and Szilagyi, U.S. Pat. No. 4,784,160, herein incorporated by reference.

Figure 6:
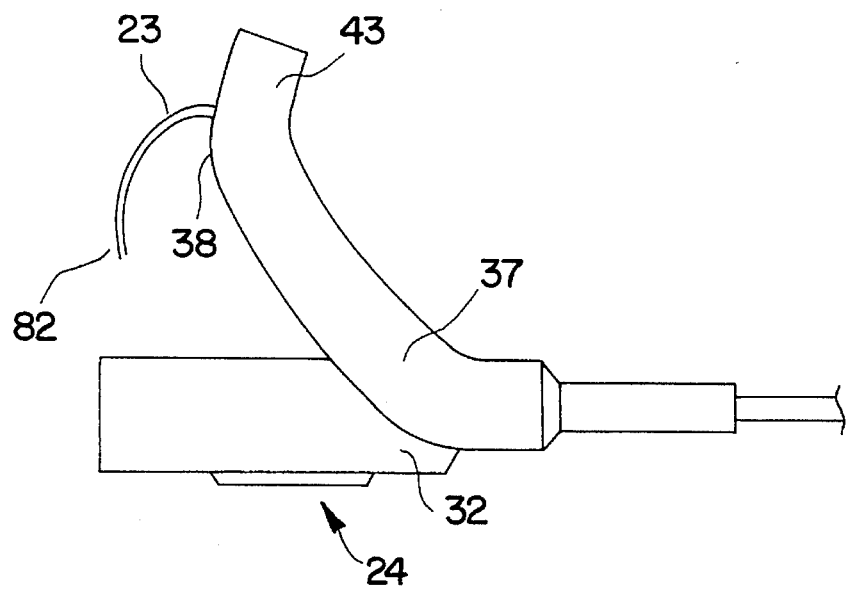
FIG. 6 is a side view of the lead head having the flexible member retracted so the lead head may be attached to the heart.

Attached at opposing regions 63, 64 of electrode mounting 32 is flexible member 43. Each of said regions 63, 64 operate as a hinge point 65 around which flexible member may rotate. Flexible member 43 is a composite structure comprising flexible beam 70 and pad spring 71. Flexible beam 70 is molded, like electrode mounting 32, from polyurethane, although other biocompatible materials may also be used, such as silicone. Pad spring 71 is a single section of spring running throughout the full perimeter of flexible member 43 from region 64 through region 81 to region 63. In FIG. 4, it is shown as being in two sections, however, for clarity. Of course a multi section pad spring 71 may also be used. Any configuration pad spring 71 may be used to provide a bias to flexible member 43 in the region of bend, shown generally as 37 in FIG. 6. In addition pad spring 71 further functions to maintain the bias of flexible member 70 from cold flow. Over time the polymer used to form flexible member 70 might tend to flow to the open position (as seen in FIG. 6.) Provision of pad spring 71 integral therewith maintains flexible member 70 in the proper orientation. Although not shown, flexible beam 70 may also feature a mesh material, preferably a DACRON polyester material or some other suitable body compatible material along bottom surface of pad. Such material would promote tissue ingrowth and thereby further lead implantation stability.

Mounted to flexible member 43 is fixation member 23. In the preferred embodiment fixation member 23 is constructed from a platinum-iridium alloy. Fixation member 23 is an integral piece having essentially two portions: root 74 and fixation portion 75. Root 74 is fitted to flexible member 43, and specifically within groove 80 in flexible beam 70. Once pad spring 71 and root 74 are positioned groove 80 may be backfilled, such as with medical adhesive or polyurethane, to anchor them in place. In region 81 root 74 runs through lumen of pad spring 71. As discussed above, fixation member is shaped for the specific application intended. An arcuate fixation member, as seen in FIG. 5, is useful for ventricular epicardial leads. A straight fixation member, as seen in FIG. 10, is useful for atrial epicardial leads. Specifically a straight fixation member fully penetrates the atrial wall. When the flexible member is released the fixation member functions to lift up the atrial wall to thereby stabilize the tissue proximate the electrode. Because the tissue movement is minimized, tissue irritation is lessened, formation of scar tissue is decreased and chronic thresholds are improved. Tips of each straight fixation member are bent (as depicted downward) to further minimize irritation of the atrial tissue.

To be precise there are two fixation portions 75, one each extending from each side of flexible member 43 and each having a tip portion 82. Through such a configuration, each fixation portion 75 follows a circular path as flexible member 43 is rotated between the positions depicted in FIG. and 5 to that shown FIG. 6, respectively, to thereby minimize tissue injury during implantation, although other shapes may also be used.

Lead head 22 is attached to cardiac tissue (not shown) as follows. Flexible member 43 is moved from its biased position, as seen in FIG. 5 to the open position as shown in FIG. 6 respectively. Flexible member 43 is configured so it may be manipulated by hand and without requiring the use of special tools, although it is also contemplated a tool may be fashioned to retain flexible member 43 to its open position, if desired. Tips 82 (only one of which is seen in FIGS. 5 and 6 due to the plan view) of each fixation member 23 are preferably sharpened. In the open position fixation member 23 is positioned above bottom surface 33 of electrode mounting 32, i.e. tips 82 of fixation member 23 are above bottom surface 33. Lead head 22 is next positioned so electrode 24 contacts heart tissue (not shown.) If acceptable results are not exhibited electrode 24 is repositioned. Once an acceptable site has been found flexible member 43 is lowered such that fixation members 23 are inserted into the tissue. Through such a design the optimal electrode position may be determined before the trauma of lead fixation is initiated.

As depicted in FIGS. 7 and 8, fixation member 23 and flexible member 43 cooperate to provide a stable fixation of lead 1 to cardiac tissue (not shown). As seen both the tip portion 82 and root portion of each embodiment of fixation member 23 are located to one side of hinge point 65. Specifically as seen in the embodiment of FIGS. 5, 9 and 10 both the tip portion 82 and root portion of each embodiment of fixation member 23 are located more distal along the lead and in the embodiment of FIG. 11 they are located more proximal along lead 1. Through such a configuration resultant force 99 from the contractile movement of heart (not shown) is limited to being perpendicular to the lead 1. Through such a configuration fixation member 23 cooperates with flexible member 43 and hinge point 65 to cause fixation member 23 to only move in pure translation due to the contractile force of the heart (as depicted in FIG. 7) or combined with a rotation of fixation member 23 in a direction which tends to move fixation member 23 deeper into the cardiac tissue (as depicted in FIG. 8.) In such a manner lead 1 is securely and reliable secured to heart. In such a manner stable fixation of lead 1 is accomplished.

Finally, while lead 1 of the present invention has been described as a unipolar lead, it should be understood the present invention could also be incorporated as a bipolar, or even multipolar lead. For example, FIG. 9 depicts a bipolar lead 1 having secondary electrode 24' spaced apart from electrode 24 and molded into bottom surface 33 of electrode mounting 32. Other configurations of secondary 24, such as a penetrating electrode, may also be used. In addition, secondary electrode 24' may further be incorporated within fixation member 23. The specific configuration if used is not within the scope of the present invention. Bipolar lead head 22 further is connected to distal end 31 of multicoil lead body 21. Multi coil lead body 21 comprises a pair of multi filer, commonly wound, separately insulated coils 25, 25' as is well known in the art. Coils 25, 25' are insulated from one another by inner insulative cover 30'. Inner insulative cover 30' is preferably made from, like insulative cover 30, a biocompatible material, such as silicone or a urethane material. As seen inner coil 25 is connected to electrode 24, as described above. Outer coil 25' is connected to secondary electrode 24'. The specific construction of multicoil lead body 21 used is not within the scope of the present invention.

FIG. 11 is a side cross-sectional view of an alternate embodiment of the present invention having the flexible member retracted so the lead head may be attached to the heart. As seen, this embodiment is substantially similar to that seen in FIGS. 5 and 6 with the exception that hinge point 65 of the flexible member is positioned at the more distal end of lead. In addition each tip of fixation member 23 features a barb 83. Barbs 83 are provided to permit better chronic fixation of lead within the heart tissue (not shown.)

While the present invention has been described in particular application to an epicardial lead, it will also be understood the invention may be practiced in lead and other electrode technologies where the aforementioned characteristics are desirable, including muscle stimulation applications as well as epimysial and vascular application. In general the stable fixation system of the present invention may be used in many other areas besides those mentioned above. Moreover, although the invention has been described in detail with particular reference to a preferred embodiments thereof, it will be understood variations and modifications can be effected within the scope of the following claims. Such modifications may include substituting elements or components which perform substantially the same function in substantially the same way to achieve substantially the same result for those described herein.

What is claimed is:

1. An epicardial lead adapted for attaching to a heart comprising:

a lead body, said lead body having a conductor and an insulating sheath, said lead body having a distal end and a proximal end;

a mounting attached to said distal end of said lead body;

an electrode attached to said mounting, said electrode further connected to said conductor, said electrode configured to contact said heart;

a flexible member connected to said mounting at a hinge point, said flexible member having a pair of fixation members mounted thereto, each said fixation member having a fixation member distal end and a fixation member root, said fixation member distal end and said root located at a point more distal along the lead body than said hinge point, said flexible member moveable between a first position and a second position wherein in said first position said distal ends of said fixation members are positioned below said electrode and in said second position said distal ends of said fixation members are positioned above said electrode.

2. A lead according to claim 1 further comprising said flexible member has means for biasing said fixable member towards said first position.

3. A lead according to claim 1 wherein each said fixation member has a fixation portion, said fixation portion is straight.

4. A lead according to claim 1 wherein each said fixation member has a fixation portion, said fixation portion is arcuate.

5. A lead according to claim 2 wherein said means for biasing comprises said flexible member having a spring therewith.

6. A lead according to claim 1 further comprising said electrode has a cavity, said cavity having a monolithic controlled release device therein.

7. A medical electrical lead adapted for attaching to tissue comprising:

a lead body, said lead body having a conductor and an insulating sheath, said lead body having a distal end and a proximal end;

a mounting attached to said distal end of said lead body;

an electrode attached to said mounting, said electrode further connected to said conductor, said electrode configured to contact said tissue;

a flexible member connected to said electrode mounting at a hinge point, said flexible member having a pair of fixation members thereto, each said fixation member having a distal end and a root, both said distal end and said root located along the lead body on a first side of said hinge point, said flexible member moveable between a first position and a second position wherein in said first position said distal ends of said fixation members are positioned below said electrode and in said second position said distal ends of said fixation members are positioned above said electrode.

8. A lead according to claim 7 further comprising said flexible member is biased towards said first position.

9. A lead according to claim 7 wherein each said fixation member has a fixation portion, said fixation portion is straight.

10. A lead according to claim 7 wherein each said fixation member has a fixation portion, said fixation portion is arcuate.

11. A lead according to claim 7 further comprising said flexible member has a spring therewith.

12. A lead according to claim 7 further comprising said electrode has a cavity, said cavity having a monolithic controlled release device therein.

* * * * *